United States Patent [19]

McNamara et al.

[11] Patent Number: 5,223,248
[45] Date of Patent: Jun. 29, 1993

[54] NON-ANTIBACTERIAL TETRACYCLINE COMPOSITIONS POSSESSING ANTIPLAQUE PROPERTIES

[75] Inventors: Thomas F. McNamara, Port Jefferson; Lorne M. Golub; Nangavarum S. Ramamurthy, both of Smithtown, all of N.Y.

[73] Assignee: The Research Foundation of State University of New York, Albany, N.Y.

[21] Appl. No.: 654,073

[22] Filed: Feb. 11, 1991

[51] Int. Cl.$^5$ .......................... A61K 7/16; A61K 31/65
[52] U.S. Cl. ........................................ 424/49; 514/152
[58] Field of Search ...................... 514/152; 424/48–58

[56] References Cited

U.S. PATENT DOCUMENTS

| | | | |
|---|---|---|---|
| 4,666,897 | 5/1987 | Golub et al. | 514/152 |
| 4,704,383 | 11/1987 | McNamara et al. | 514/152 |
| 4,925,833 | 5/1990 | McNamara et al. | 514/152 |
| 4,935,411 | 6/1990 | McNamara et al. | 514/152 |
| 4,935,412 | 6/1990 | McNamara et al. | 514/152 |

OTHER PUBLICATIONS

Golub et al., "Further Evidence That Tetracyclines Inhibit Collagenase Activity In Human Crevicular Fluid and From Other Mammalian Sources", *J. Periodont. Res.* 20, 12–23 (1985).

*The Chemistry of Tetracyclines*, (L. A. Mitscher, ed.) Chapter 6, pp. 165–218 (1978).

Golub et al., "Tetracyclines (TCs Inhibit Metalloproteinase (MPs): In Vitro Effects In Arthritic and Diabetic Rats, and New *In Vitro* Studies", Abstract, Matrix Metalloproteinase Conference, p. 43, Sep., 1989.

Sipos et al., "The Effect of Collagenase Inhibitors on Alveolar Bone Loss Due to Periodontal Disease in Desalivated Rats", Abstract, Matrix Metalloproteinase Conference, p. 48, Sep., 1989.

Elewski, et al., "In Vitro Suppression of Neutrophil Chemotaxis by Systemically and Topically Administered tetracycline", *Journal of the American Academy of Dermatology*, 8, 807–812 (1983).

Golub et al., "Low–dose Doxycycline Therapy: Effect on Gingival and Crevicular Fluid Collagenase Activity in Humans", *Journal of Periodonal Research*, 25, 321–330 (1990).

Golub et al., "In Vivo Crevicular Leukocyte Response To A Chemotactic Challenge: Inhibition by Experimental Diabetes", *Infection and Immunity* 37, 1013–1020 (1982).

Yu et al., "Serum Levels of Chemically-Modified tetracycline (CMT): A Comparison To Tetracycline (TC)", *J. Dent. Res.* 69, 245 (Special Issue) IADR Abstract No. 1092.

*Primary Examiner*—Shep K. Rose
*Attorney, Agent, or Firm*—Hoffmann & Baron

[57] ABSTRACT

A method of inhibiting plaque formation on mammalian tooth surfaces is disclosed. The method includes contacting the tooth surfaces with an effective amount of a non-antibacterial tetracycline. In a preferred embodiment, such tetracyclines are included in various oral hygiene products such as dentifrices, lozenges, chewing gums and the like to contact the tooth surfaces and prevent plaque accumulation thereon.

11 Claims, 4 Drawing Sheets

NON-ANTIBACTERIAL TETRACYCLINE COMPOSITIONS POSSESSING ANTIPLAQUE PROPERTIES

BACKGROUND OF THE INVENTION

The present invention relates to methods of inhibiting plaque formation on hard and soft tissue surfaces. In particular, the present invention relates to preventing dental plaque formation using non-antibacterial tetracyclines.

For several decades now, there has been an increased awareness of the relationship between plaque formation on tooth surfaces and dental cavities or caries. Dental plaque is generally regarded as a film of bacteria, bacterial polymers, salivary polymers, remnants of epithelial cells and leukocytes. The bacteria, principally *Streptococcus mutans*, is part of the naturally occurring microflora of the oral cavity. The bacteria use natural sugars such as sucrose and glucose included in the diet as a nutrition source and produce cement-like polymers which bind to the enamel tooth surface. Once bound, the opportunistic bacteria cause demineralization of the enamel by secreting acids and ultimately caries. Although the roots of teeth lack enamel, plaque formation may also be found below the gingival margin. Such plaque formation ultimately leads to root caries, a leading cause of tooth loss in adults. Root caries can be especially prevalent when, due to periodontal disease, the gums and alveolar bone both recede and expose the roots.

In the past, most efforts aimed at reducing plaque formation and dental caries have included reducing sugar intake, regular brushing, flossing and periodic removal of the plaque by dental professionals.

In some cases, plaque formation on tooth surfaces may become excessive and even pathologic. In these situations, it is often necessary to institute prophylactic measures in addition to those described above. In the past, broad spectrum antibiotics such as tetracyclines and metronidazole have been used in the treatment of periodontal disease to reduce oral cavity microflora, which is the most virulent aspect of plaque formation. Although antibiotic agents are effective in reducing the bacteria responsible for plaque formation, extended periods of antibiotic administration are avoided due to high incidences of side effects. Side effects most often associated with long-term antibacterial agent usage include intestinal disturbances, overgrowth of yeast and fungi, and most importantly, the development of antibiotic-resistant bacterial strains.

As stated above, tetracyclines are broad spectrum antibiotics and are active against most oral cavity microflora. The tetracycline compound exhibits the following general structure:

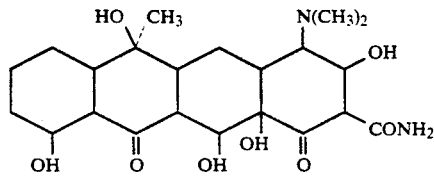

The numbering system of the ring nucleus is as follows:

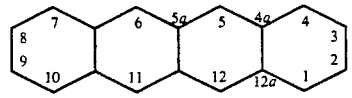

The tetracycline molecule is amenable to substantial modification without losing its antibiotic properties. Examples of modifications that may and may not be made to the basic tetracycline structure have been reviewed by Mitscher in the *Chemistry of Tetracyclines*, Chapter 6. According to Mitscher, the substituents at positions 5-9 of the tetracycline ring may be modified without complete loss of antibiotic properties. Changes to the basic ring system or replacement of the substituents at positions 1-4 and 10-12, however, generally lead to synthetic tetracyclines having substantially less or effectively no antibacterial activity. For example, 4-dedimethylaminotetracycline is commonly considered to be a non-antibacterial tetracycline.

Various properties of antimicrobial and non-antimicrobial tetracyclines are known. For example, it is known that antimicrobial and non-antimicrobial tetracyclines can bind to metal ions such as calcium. Tetracyclines are also known inhibitors of collagen destructive enzymes such as mammalian collagenase, a calcium dependent zinc-metalloproteinase. Collagen is a major component of connective tissue matrices such as those in the bone, synovium, eye, skin, tendons and gingiva but not tooth surface enamel.

U.S. Pat. No. 4,666,897 to Golub, et al. discloses tetracyclines, including commercially-available antimicrobial forms of the drug, inhibit excessive bone resorption and collagenolytic enzyme activity. U.S. Pat. No. 4,704,383 to McNamara, et al. discloses tetracyclines having substantially no effective antibacterial activity inhibiting collagenolytic enzyme activity in rats. Moreover, McNamara, et al. also disclose that non-antimicrobial tetracyclines reduce bone resorption in organ culture.

Although some oral hygiene products such as dentifrices have been recently introduced to combat the problem of plaque formation, a complete solution remains elusive.

In view of the desire to reduce plaque formation on tooth surfaces and further in view of the desire to avoid using antimicrobial antibiotics to accomplish this result, it is an object of the present invention to provide an improved method of inhibiting plaque formation on tooth surfaces.

It is a further object of the present invention to provide a method of inhibiting plaque formation on tooth surfaces using non-antibacterial tetracyclines.

SUMMARY OF THE INVENTION

In accordance with the present invention, it has been surprisingly found that tetracyclines inhibit plaque formation on tooth surfaces in a manner completely separate from antibacterial eradication of the oral cavity microflora. The method includes contacting the tooth surfaces with an effective amount of a non-antimicrobial tetracycline which results in the prevention of plaque formation and colonization on tooth surfaces.

The non-antimicrobial tetracyclines useful in the present invention are preferably chemically modified tetracyclines (CMT's) such as dedimethylaminotetracyclines. Examples of such preferred tetracyclines include 4-dedimethylaminotetracycline, 4-dedimethylamino-5-oxytetracycline, 6-deoxy-6-demethyl-4-dedimethylaminotetracycline, 7-chloro-6-demethyl-4-dedimethylaminotetracycline and 6-α-deoxy-5-hydroxy-4-dedimethylaminotetracycline. Other suitable CMT's include, for example, 6-α-benzylthiomethylenetetracycline, the mono-N-alkylated amide of tetracycline, 6-fluoro-6-demethyltetracycline, tetracyclinonitrile, 4-hydroxy-4-dedimethylaminotetracycline and 11α-chlortetracycline.

The amount of the non-antimicrobial tetracycline used in the method of the present invention may be generally described as that amount which effectively inhibits plaque formation on tooth surfaces. For example, a non-antimicrobial tetracycline, may be included in dentifrices, mouthwashes or similar oral hygiene preparations in amounts ranging from about 10 mg% to about 100 mg%. In a preferred embodiment, the non-antimicrobial tetracycline is included in amounts of from about 15 mg% to about 25 mg%, with concentrations of about 20 mg% being most preferred. When contacting tooth surfaces at these concentrations and for time periods typical for the oral hygiene product selected to contain the non-antimicrobial tetracycline, the non-antibacterial tetracyclines described herein prevent plaque formation on tooth surfaces. Naturally, the amount of the various tetracycline analogues will vary somewhat from each other and the ranges is set forth above are only illustrative of all possible dosage choices. Those skilled in the art will determine optimal concentrations for the desired non-antimicrobial tetracycline from clinical experience in order to carry out the present method.

As a result of the present invention, significant improvements in oral hygiene are realized. By eliminating the adhesion of plaque to tooth surfaces, the destructive activity caused by normal mouth flora is significantly reduced. Moreover, the reduction of plaque formation on tooth surfaces is realized not only on the enamel area above the gingival margin but also on the root surfaces below the gingival margin. Thus, the method of the present invention's prevention of plaque formation on tooth surfaces removes a critical step in the pathologic process of tooth decay. Since the method of the present invention includes non-antimicrobial tetracyclines, the inhibition of plaque formation on tooth surfaces is achieved without using antimicrobial agents. Thus, the oral microflora remains intact. Antimicrobially-resistant strains of organisms, gastrointestinal disturbances, yeast and fungi overgrowth which are associated with antimicrobial therapy are also beneficially avoided.

For a better understanding of the present invention, together with other and further objects, references made to the following description and its scope will be pointed out in the appended claims.

DETAILED DESCRIPTION OF THE INVENTION

Figure 1:
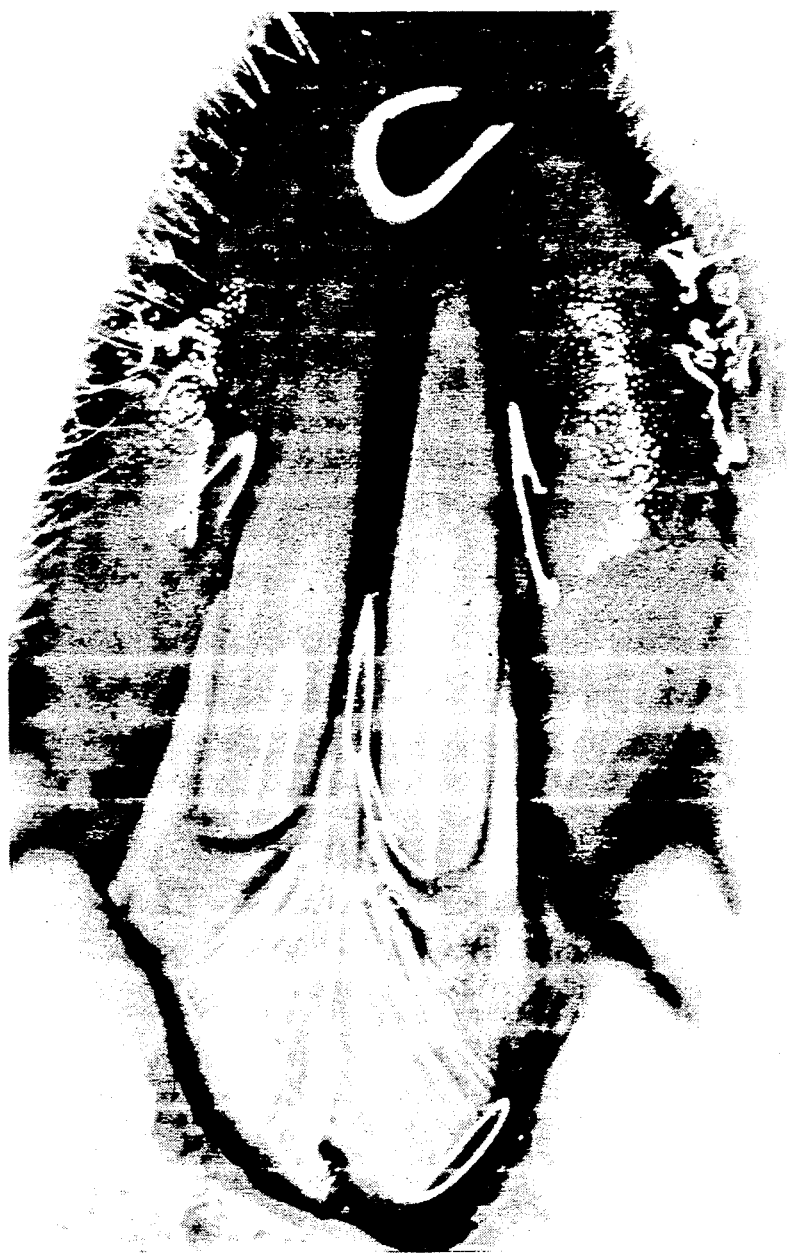
FIG. 1 is a photograph showing the gum area, gingival margin and lower incisors of a non-diabetic control Osaka Dental University (ODU) rat.

In accordance with the present invention, a method for preventing plaque formation on tooth surfaces is disclosed. The method includes contacting tooth surfaces with an effective amount of a non-antimicrobial tetracycline which prevents plaque formation.

The non-antimicrobial tetracyclines useful in carrying out the method of the present invention may be described as chemically modified tetracyclines (CMT's). For purposes of the present invention, CMT designates a tetracycline molecule which has been modified to essentially eliminate antimicrobial properties. Methods for altering and eliminating the antimicrobial properties of a tetracycline are disclosed in the *Chemistry of Tetracyclines*, Chapter 6, Mitscher, Ed., at page 211. As pointed out by Mitscher, modifications of the tetracycline molecule at positions 1, 2, 3, 4, 10 and 12a can lead to loss of antimicrobial activity.

Examples of such preferable tetracyclines include those lacking the dimethylamino side chain at position 4. Such chemically modified tetracyclines (or CMT's) include, for example, 4-dedimethylaminotetracycline, 4-dedimethylamino-5-oxytetracycline, 4-dedimethylamino-7-chlortetracycline, 4-hydroxy-4-dedimethylaminotetracycline, 6-demethyl-6-deoxy-4-dedimethylaminotetracycline, and 6-α-deoxy-5-hydroxy-4-dedimethylaminotetracycline.

Further examples of tetracyclines modified for reduced antimicrobial activity include 6-α-benzylthiomethylenetetracycline, the mono-N-alkylated amide of tetracycline, 6-fluoro-6-demethyltetracycline, 11α-chlortetracycline and tetracyclinonitrile.

In accordance with the present invention, the amount of the tetracycline required to inhibit dental plaque formation on tooth surfaces is an amount which is effectively non-antimicrobial yet is effective in inhibiting plaque formation and plaque adhesion on tooth surfaces. The amount of non-antimicrobial tetracycline may also be described as a range. The highest amount is that amount which does not cause clinically detrimental side effects. For the purpose of the present invention, side effects would include any untoward reaction which would clinically warrant ceasing the tetracycline's administration. Such side effects include, for example, symptoms of toxicity. The lowest amount is that minimum amount which produces the desired result of preventing plaque formation on tooth surfaces.

For illustrative purposes, non-antimicrobial tetracyclines may be included in vehicles such as dentifrices, mouthwashes, chewing gums, lozenges, confections or other suitable dental hygiene preparations to carry out the method of the present invention. In such embodiments, the tetracycline may be included in an amount of from about 10 mg% to about 100 mg%. In a preferred embodiment, the non-antimicrobial tetracycline may be present in amount of from about 15 mg% to about 25 mg%. In a most preferred embodiment, the non-antimicrobial tetracycline is present in an amount of about 20 mg%. The method of the present invention may then be carried out by using one of the dental hygiene products described above containing a non-antimicrobial tetracycline to contact the tooth surfaces for a sufficient time to inhibit plaque formation.

The time required for the non-antimicrobial tetracycline to contact the tooth surface and effectively inhibit plaque formation is conveniently the same amount of time as one is accustomed to for using oral hygiene products. For example, if the non-antimicrobial tetracycline is included in a toothpaste, normal brushing one to three times daily is sufficient. Similarly, contacting the teeth with an oral rinse containing the tetracycline for normal periods of around a minute before expectorating one to three times daily would achieve the same result.

Tests were conducted using the method of the present invention's prevention of plaque formation on tooth surfaces. The tests demonstrate the effectiveness and unexpected ability of non-antimicrobial tetracyclines to prevent plaque adhesion on tooth surfaces without antibiotic effect on oral flora.

EXAMPLES

The following Examples serve to provide further appreciation of the invention, but are not, in any way, to be considered restrictive of the effective scope of the invention.

Example I

In this Example, the lack of antimicrobial effect of CMT on crevicular microflora was demonstrated using a group of six adult Osaka Dental University (ODU) rats. When rendered diabetic, these rats exhibit large plaque accumulations on their lower incisor teeth. Two rats were preserved as nondiabetic controls, while the remaining four rats were made diabetic by injection of 70/mg/kg of the diabetogenic agent streptozotocin according the method set forth, for example, by Golub et al. in *Infect. Immun.* 37:1013 (1982).

The diabetic rats were then further divided into two groups. One group was given 57 mg/kg/day of the CMT, 4-dedimethylaminotetracycline, which was incorporated into the rat's daily food intake. The second diabetic group was left untreated.

After 21 days, the rats were sacrificed and samples of the crevicular microflora were removed from each of the rats in all groups and transferred to a brain-heart infusion-supplemented broth and incubated for 72 hours at 37° C.

At the end of this incubation period, the microflora from each group of rats was compared to determine if any changes in the microflora were attributable to 4-dedimethylaminotetracycline. The results are summarized in Table 1.

Table 1 shows the presence and/or absence of various bacteria found in the microflora of the oral cavity of the ODU rats. Changes in the makeup of the microflora found in each group are shown below.

TABLE 1

| Organisms | Non-diabetic Control | Diabetic Untreated | Diabetic 4-dedimethyl-aminotetracycline |
|---|---|---|---|
| *E. coli* | + | + | + |
| Bacteroides | + | − | − |
| Fusobacterium | + | + | + |
| Proteus | + | − | − |
| Veillonella | + | + | + |
| Leptotrichia | + | − | − |
| Streptococcus | | | |
| alpha hemolytic | − | − | − |
| beta hemolytic | − | − | − |

TABLE 1-continued

| Organisms | Non-diabetic Control | Diabetic Untreated | Diabetic 4-dedimethyl-aminotetracycline |
|---|---|---|---|
| gamma hemolytic | + | + | + |
| Actinomyces | + | + | + |
| Lactobacillus | + | − | + |
| Staphylococcus | − | + | + |
| Bifidobacterium | + | − | − |
| Candida | − | (±) | − |

+ = present
− = not present

Referring now to Table 1, the results of the isolation and identification of the organisms show that the untreated diabetic control animals and those treated with 4-dedimethylaminotetracycline had essentially the same oral flora. Moreover, the bacterial composition and amount of growth obtained from both the diabetic control rats and the diabetic rats receiving 4-dedimethylaminotetracycline were essentially indistinguishable. These results, therefore, demonstrate the lack of antibacterial activity associated with 4-dedimethylaminotetracycline.

Thus, it can be seen that CMT's such as dedimethylaminotetracycline have essentially no antimicrobial effect on the crevicular microflora. Moreover, CMT's also demonstrate essentially no microflora altering effects. Therefore, any prevention of plaque adhesion to tooth surfaces by CMT's cannot be attributed to antimicrobial or microflora altering properties of the CMT.

Example II

In this Example, the in vivo effect of non-antimicrobial tetracyclines on plaque accumulation on incisors was demonstrated. Thirty-two adult male ODU rats were distributed into four groups of eight. As was done in Example I, one group of rats was preserved as a non-diabetic control and the remaining rats were made diabetic by injection with streptozotocin. One group of diabetic rats was not treated further and designated the diabetic control. The second group of diabetic rats was given approximately 20 mg of the antimicrobial tetracycline hydrochloride in their daily meal. The last group of diabetic rats was treated by including approximately 20 mg of CMT as part of their daily meal.

After a 3-week protocol, the rats were anesthetized with halothane. The jaws of each rat were gently propped open, and the lower incisor teeth were flushed with distilled water to remove loose debris. The teeth were then stained with a plaque-disclosing solution (erythrocin R) to determine the presence of plaque on the incisor. The results are set forth below and in FIGS. 1-4.

Results

Figure 2:
FIG. 2 is a photograph showing the gum area, gingival margin and lower incisors of an untreated diabetic ODU rat with extensive plaque formation on the incisors and on the gums.
Figure 3:
FIG. 3 is a photograph showing the gum area, gingival margin and lower incisors of a diabetic ODU rat after having been treated with oral daily doses of the antimicrobial agent, tetracycline hydrochloride.
Figure 4:
FIG. 4 is a photograph showing the gum area, gingival margin and lower incisors of a diabetic ODU rat after having been treated with oral daily doses of the non-antimicrobial tetracycline, 4-dedimethylaminotetracycline.

Referring now to FIG. 1, it can be seen that the non-diabetic control ODU rats showed no detectable plaque accumulation on their lower incisors at or near the gingival margin. As can be seen in FIG. 2, the untreated diabetic ODU rats showed large accumulations of dental plaque on the incisors extending to and including the gingiva. In FIGS. 3-4, it can be seen that the rats in both the antimicrobial and non-antimicrobial tetracycline-treated groups showed significant reductions in plaque accumulation on the lower incisors when compared to the untreated diabetic group. It was also observed that the lower incisors of the rats in the dedimethylaminotetracycline-treated group greatly resembled those of the non-diabetic control rats which normally do not develop excessive plaque formation on their tooth surfaces.

It can be seen, therefore, that non-antimicrobial tetracyclines inhibit microbially-mediated dental plaque accumulation on teeth in vivo by a mechanism independent of antimicrobial properties of tetracyclines.

Example III

In this Example, further evidence of non-antimicrobial tetracyclines ability to inhibit plaque formation was demonstrated. Tiles made of polymethylmethacrylate, which is used for dentures, and has a surface which approximates the enamel of teeth for plaque adherence purposes were selected. Ten tiles were incubated in test tubes with a plaque-forming solution containing sucrose, fresh saliva, $K^+$, $Ca^{++}$, $Na^+$, $Cl^-$ and $F^-$ ions, a buffer containing $Na_2 HPO_4 7H_2O$ $NaHCO_3$, and a culture of oral cavity microflora obtained from a patient at the University of New York Dental School Clinic at Stony Brook, N.Y. which had been incubated for three days at 37° C. Half of the test tubes were incubated with 20 mg% or 0.02% by weight of 4-dedimethylaminotetracycline to demonstrate its effectiveness against plaque formation, while the other half were maintained as untreated controls. After the 3-day incubation, each tile was removed from the test tube and all non-adherent material was rinsed away with distilled water. The tiles were then air-dried and any bacterial plaque adhering to the tiles was stained by dipping the tiles into a solution of Basic Fuchsin. The amount of stain on the tile provides a direct correlation to plaque formation. Each tile was then destained in a solution of 5% EDTA in 50% 2-propanol. An aliquot of the destaining solution was then measured for light adsorbence at 550 nm in a Spect. 70 colorimeter and compared to an aliquot from the untreated tiles. The results are set forth below in Table 2.

TABLE 2

|  | Spect. 70 Colorimeter Absorbance |
|---|---|
| Untreated Tiles | 0.513 |
| Treated Tiles (0.02% CMT) | 0.330 |
| Difference | 36% |

As can be seen from the above Example, the method of the present invention provides significant advantages and improvements in the inhibition of plaque formation on tooth surfaces. Furthermore, by contacting tooth surfaces with an effective amount of a non-antimicrobial tetracycline, bacterial plaque formation can be significantly inhibited in the oral cavity.

Examples IV-VIII

In these Examples, various oral hygiene products containing non-antimicrobial tetracyclines are set forth. In each of the products, the term "CMT" is used to designate a chemically modified tetracycline such as a dedimethylamino-tetracycline which essentially lacks antimicrobial activity. Each of the following illustrative products is useful in providing a vehicle for allowing an effective amount of the tetracycline to contact the tooth surface and thereby inhibit plaque formation.

Example IV

| Tooth Powder | |
|---|---|
| Ingredient | wt % |
| Silica hydrogel | 96.10 |
| Zinc chloride | 0.50 |
| Sodium fluoride | 0.22 |
| Sodium gluconate | 0.27 |
| Synthetic sweetener (saccharin/aspartame) | 0.50 |
| Sodium methyl cocoyltaurate | 1.50 |
| Flavoring | 0.80 |
| CMT | 0.01–0.10 |

Example V

| Lozenge | |
|---|---|
| Ingredient | wt % |
| Sorbitol powder | 74.50 |
| Corn syrup | 15.00 |
| Zinc chloride | 0.50 |
| Sodium fluoride | 0.22 |
| Flavor and color | 1.15 |
| Sodium gluconate | 0.30 |
| Synthetic sweeteners | 0.20 |
| Tableting lubricant | 5.00 |
| Deionized water | 3.00 |
| CMT | 0.01–0.10 |

Example VI

| Chewing Gum | |
|---|---|
| Ingredient | wt % |
| Gum base | 30.00 |
| Sorbitol | 48.85 |
| Corn syrup | 15.00 |
| Flavor | 1.50 |
| Zinc chloride | 0.50 |
| Sodium fluoride | 0.22 |
| Sodium gluconate | 0.30 |
| Gum tragacanth | 0.50 |
| Deionized water | 3.00 |
| CMT | 0.01–0.10 |

Example VII

| Dentifrice Composition | |
|---|---|
| Ingredient | wt % |
| Glycerin | 25.00 |
| Zeo 49B (Silicone Dioxide) | 21.50 |
| HMP (Hexaphos) | 6.00 |
| Syloid 244 (synthetic silica) | 3.00 |
| Sodium Lauryl Sulfate | 1.20 |
| Flavor | 1.00 |
| Sodium Hydroxide (50% Solution) | 1.00 |
| Xanthan Gum | 1.00 |
| Sodium Benzoate | 0.50 |
| Titanium Dioxide | 0.50 |
| Sodium Saccharin | 0.30 |
| Sodium Fluoride | 0.22 |
| CMT | 0.01–0.10 |
| Deionized water to Q.S. | 100 |

Example VIII

| Mouthwash | |
|---|---|
| Ingredient | wt % |
| Ethyl Alcohol | 15.0 |
| Glycerol | 10.0 |
| Flavor | 0.4 |
| Sodium saccharin | 0.03 |
| Sodium Fluoride | 0.05 |
| Pluronic F 108 | 2.0 |
| CMT | 0.01–0.10 |
| Deionized Water to Q.S. | 100 |

Other formulations for self-treatment as well as professional treatment can be provided by skilled artisans. The present invention provides a highly effective and reliable anti-plaque agent and treatment which can be used without incurring unwanted side effects which can result from antibacterial tetracycline.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A method of treating mammalian tooth surfaces to prevent adhesion of dental plaque comprising contacting said tooth surfaces with an effective amount of a non-antimicrobial tetracycline.

2. The method according to claim 1, wherein said non-antimicrobial tetracycline is a 4-dedimethylaminotetracycline.

3. The method according to claim 2, wherein said dedimethylaminotetracycline is selected from the group consisting of 4-de(dimethylamino)-tetracycline, 4-de(dimethylamino)-5-oxytetracycline, 4-de(dimethylamino)-7-chlortetracycline, 4-hydroxy-4-dedimethylaminotetracycline, 6-demethyl-6-deoxy-4-dedimethylaminotetracycline, and 6-$\alpha$-deoxy-5-hydroxy-4-dedimethylaminotetracycline.

4. The method according to claim 3, wherein said tetracycline is selected from the group consisting of 6$\alpha$-benzylthiomethylenetetracycline, the mono-N-alkylated amide of tetracycline, 6-fluoro-6-demethyltetracycline, 11$\alpha$a-chlortetracycline and tetracyclinonitrile.

5. The method of claim 4, wherein said non-antimicrobial tetracycline is present in an amount of from about 10 mg% to about 100 mg% by weight.

6. The method of claim 5, wherein said non-antimicrobial tetracycline is present in an amount of from about 15 mg% to about 25 mg%.

7. The method of claim 6, wherein said non-antimicrobial tetracycline is present in an amount of about 20 mg%.

8. The method of claim 4, wherein said non-antimicrobial tetracycline incorporated into a dentifrice.

9. The method of claim 4, wherein said non-antimicrobial tetracycline is incorporated into a lozenge.

10. The method of claim 4, wherein said non-antimicrobial tetracycline is incorporated into a chewing gum.

11. The method of claim 4, wherein the non-antimicrobial tetracycline is contained in a mouthwash or oral rinse product.

* * * * *